(12) United States Patent
Li et al.

(10) Patent No.: US 11,965,196 B2
(45) Date of Patent: Apr. 23, 2024

(54) ENZYMATIC PREPARATION METHOD OF INCLUSION COMPLEXES OF TRIBUTYRIN

(71) Applicant: Jiangnan University, Wuxi (CN)

(72) Inventors: Caiming Li, Wuxi (CN); Zhaofeng Li, Wuxi (CN); Shuangdi Chen, Wuxi (CN); Zhengbiao Gu, Wuxi (CN); Yan Feng, Wuxi (CN); Zexi Li, Wuxi (CN); Li Cheng, Wuxi (CN); Yan Hong, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 827 days.

(21) Appl. No.: 17/034,234

(22) Filed: Sep. 28, 2020

(65) Prior Publication Data
US 2021/0010044 A1 Jan. 14, 2021

Related U.S. Application Data

(63) Continuation of application No. PCT/CN2018/089940, filed on Jun. 5, 2018.

(30) Foreign Application Priority Data

Apr. 18, 2018 (CN) .......................... 2018103471067

(51) Int. Cl.
| | | |
|---|---|---|
| *C12P 19/04* | (2006.01) | |
| *A23K 10/14* | (2016.01) | |
| *A23K 20/158* | (2016.01) | |
| *A23K 20/163* | (2016.01) | |
| *A23K 40/30* | (2016.01) | |
| *A61K 9/107* | (2006.01) | |
| *A61K 31/19* | (2006.01) | |
| *A61K 47/69* | (2017.01) | |
| *C12P 19/18* | (2006.01) | |

(52) U.S. Cl.
CPC .............. *C12P 19/04* (2013.01); *A23K 10/14* (2016.05); *A23K 20/158* (2016.05); *A23K 20/163* (2016.05); *A23K 40/30* (2016.05); *A61K 9/107* (2013.01); *A61K 31/19* (2013.01); *A61K 47/6951* (2017.08); *C12P 19/18* (2013.01)

(58) Field of Classification Search
CPC ....... C12P 19/04; A23K 10/14; A23K 20/158; A23K 20/163; A23K 40/30; A23K 50/10; A23K 50/30; A23K 50/75; A61K 9/107; A61K 47/6951; A23V 2002/00
See application file for complete search history.

(56) References Cited

U.S. PATENT DOCUMENTS

| | | | | |
|---|---|---|---|---|
| 4,921,796 A | * | 5/1990 | Rozzell ................ | C12N 9/1074 435/97 |
| 5,376,537 A | * | 12/1994 | Cami ...................... | C12P 19/18 435/97 |
| 10,098,964 B2 | * | 10/2018 | Donovan ................ | A23L 33/15 |

FOREIGN PATENT DOCUMENTS

| | | |
|---|---|---|
| CN | 2574431 Y | 9/2003 |
| CN | 101301030 A | 11/2008 |
| CN | 101319243 A | 12/2008 |
| CN | 103243140 A | 8/2013 |
| CN | 104106734 A | 10/2014 |
| CN | 104509701 A | 4/2015 |
| CN | 105746905 A | 7/2016 |
| CN | 106480133 A | 3/2017 |

OTHER PUBLICATIONS

Devos et al., Practical limits of function prediction. Proteins: Structure, Function, and Genetics. 2000, vol. 41: 98-107. (Year: 2000).*
Donovan et al., Microencapsulation of Tributyrin to Improve Sensory Qualities and Intestinal Delivery. Ph D., Thesis, Univ. of Illinois, Urbana-Champaign, 2015, pp. 1-291. (Year: 2015).*
Li et al., Inclusion of tributyrin during enzymatic synthesis of cyclodextrins by β-cyclodextrin glycosyltransferase from Bacillus circulans. Food Hydrocolloids, 2020, vol. 99, 105336, pp. 1-7. (Year: 2020).*
Melzer et al., Stepwise error-prone PCR and DNA shuffling changed the pH activity range and product specificity of the cyclodextrin glucanotransferase from an alkaliphilic *Bacillus* sp. FEBS Open Bio., 2015, vol. 5: 528-534. (Year: 2015).*
Tao et al., Improved production of cyclodextrin glycosyltransferase from Bacillus stearothermophilus NO2 in *Escherichia coli* via directed evolution. Appl. Microbiol. Biotechnol., 2020, vol. 104: 173-185. (Year: 2020).*
Whisstock et al., Prediction of protein function from protein sequence. Q. Rev. Biophysics., 2003, vol. 36 (3): 307-340. (Year: 2003).*
Wind et al., Cyclodextrin Formation by the Thermostable a-Amylase of Thermoanaerobacterium thermosulfurigenes EM1 and Reclassification of the Enzyme as a Cyclodextrin Glycosyltransferase. Appl. Environ. Microbiol., 1995, vol. 61(4): 1257-1265 (Year: 1995).*

\* cited by examiner

Primary Examiner — Ganapathirama Raghu
(74) Attorney, Agent, or Firm — IPRO, PLLC

(57) ABSTRACT

The disclosure relates to an enzymatic preparation method of inclusion complexes of tributyrin, and belongs to the technical field of oil microencapsulation. The disclosure combines enzymatic synthesis of cyclodextrin and inclusion of tributyrin with cyclodextrin, including enzymatic preparation of cyclodextrin with a CGT enzyme. Tributyrin is added in the preparation process; after reaction, Tween is added, and homogenization and spray drying are carried out. The effect of the finally obtained tributyrin powder is much better than that of single inclusion of tributyrin with cyclodextrin. The disclosure is simple in process, low in cost and convenient in operation; reaction processes are free of toxicity and pollution; there are no toxic reagent residues; the inclusion effect is obvious, and better utilization of a nutritional additive tributyrin in actual production is facilitated.

8 Claims, 4 Drawing Sheets

ENZYMATIC PREPARATION METHOD OF INCLUSION COMPLEXES OF TRIBUTYRIN

TECHNICAL FIELD

The disclosure relates to an enzymatic preparation method of inclusion complexes of tributyrin, and belongs to the technical field of oil microencapsulation.

BACKGROUND

Tributyrin (glycerin tributyrate, $C_{15}H_{26}O_6$) is obtained by esterifying three molecules of butyric acid and one molecule of glycerin. Butyric acid, as one of short-chain fatty acids, has the advantages and functions of being environmentally friendly, safe to use, capable of improving animal production performance and maintaining intestinal structural integrity and the like, and therefore is considered as a potential substitute for antibiotic feed additives. However, there are many problems in the actual application process, including easy dissociation, volatility, special smell, short half-life and the like. As the precursor of butyric acid, tributyrin is long in half-life, convenient to use, safe and free of toxic and side effects; not only solves the problem that liquid butyric acid is volatile and difficult to add, but also overcomes the shortcoming of unpleasant smell when butyric acid is used directly; has the functions of promoting the healthy development of the intestinal tracts of livestock and poultry, improving the immunity of the body, promoting the digestion and absorption of nutrients and the like; and plays an important role in regulating metabolism and maintaining the body health of animals. Therefore, tributyrin has become a good nutritional additive product at present.

Cyclodextrin is a cyclic oligosaccharide obtained after cyclodextrin glucosyltransferase (CGTase) acts on glucan polymers such as starch, glycogen and malto-oligosaccharide through a cyclization reaction. Cyclodextrin is formed by connecting 6 or more D-glucopyranoses with α-1,4-glycosidic bonds. Common cyclodextrins are α-cyclodextrin, β-cyclodextrin and γ-cyclodextrin, which are formed by the connection of 6, 7 and 8 glucose units respectively. These three cyclodextrins are also the most widely used cyclodextrins in the industry at present. Due to the slightly cone-shaped hollow cylindrical structure, cyclodextrin has the characteristics of external hydrophilicity and internal hydrophobicity, so that cyclodextrin can form inclusion complexes with many hydrophobic guest molecules, and thus the physical and chemical properties, such as solubility, volatility and chemical properties, of the guest molecules can be changed. At the same time, α-cyclodextrin, β-cyclodextrin and γ-cyclodextrin are acid-resistant, heat-resistant, alkali-resistant, non-hygroscopic, free of fixed melting point and good in thermal stability.

Although tributyrin has a higher potential application value than butyric acid and salts thereof, tributyrin also has the problems of peculiar smell and poor fluidity. Cyclodextrin, having the characteristic of a special cavity, is used to include tributyrin and can effectively improve the dispersibility and fluidity, mask the peculiar smell and prolong the shelf life of tributyrin. However, if a cyclodextrin product is directly used as the wall material for inclusion of tributyrin, there are disadvantages such as high cost, low oil content and poor solubility. There is no report about combing the inclusion of tributyrin and the production process of cyclodextrin at present.

SUMMARY

In view of the problems in the background, the disclosure provides an enzymatic preparation method of inclusion complexes of tributyrin. According to the disclosure, by combining the processes of enzymatic synthesis of cyclodextrin and inclusion of tributyrin with cyclodextrin, tributyrin is added in the process of enzymatic preparation of cyclodextrin with the CGT enzyme; after reaction, an emulsifier is added, and homogenization and spray drying are carried out, so that the cost is reduced.

The disclosure provides an enzymatic preparation method of inclusion complexes of tributyrin. According to the method, starch milk or a maltodextrin solution is used as a raw material. The mass concentration of the starch milk or maltodextrin solution is 15% to 30%. An enzyme is added into the starch milk or maltodextrin solution for liquefaction reaction and cyclization reaction, and tributyrin and an emulsifier are added after the cyclization reaction is completed, so that tributyrin is included.

In an embodiment of the disclosure, starch in the starch milk is one or more of corn starch, waxy corn starch, potato starch, rice starch, cassava starch and wheat starch, and the maltodextrin is maltodextrin from the starch source with a DE value of 5 to 25.

In an embodiment of the disclosure, steps of the method sequentially include the liquefaction reaction, the cyclization reaction, mixing emulsification, shearing, homogenization and spray drying.

In an embodiment of the disclosure, the enzyme is cyclodextrin glucosyltransferase.

In an embodiment of the disclosure, the mass ratio of tributyrin to the starch or maltodextrin is (0.30-0.75):1.

In an embodiment of the disclosure, in the liquefaction reaction, the addition amount of cyclodextrin glucosyltransferase is 2-4 U/g starch or maltodextrin wet substrate; the liquefaction temperature is 80-90° C.; and the liquefaction reaction time is 30-60 minutes.

In an embodiment of the disclosure, in the cyclization reaction, the addition amount of cyclodextrin glucosyltransferase is 2-4 U/g starch or maltodextrin wet substrate; the cyclization temperature is 45° C.; and the cyclization reaction time is 8-12 hours.

In an embodiment of the disclosure, the emulsifier is any one or more of Tween, arabic gum, xanthan gum and the like, and the mass ratio of the emulsifier to the starch or maltodextrin is (0.3-0.5):1.

In an embodiment of the disclosure, in the method, the shearing speed is 8000-20000 rpm, and the shearing time is 2-5 minutes; the homogenization pressure is 30-40 MPa, and the homogenization frequency is 2-3; the spray drying conditions are: the air inlet temperature is 180-185° C.; the air outlet temperature is 85-95° C.; and the feeding flow rate is 20-22 mL/min.

In an embodiment of the disclosure, the method sequentially includes the six steps of liquefaction reaction, cyclization reaction, mixing emulsification, shearing, homogenization and spray drying:

(1) 2-4 U/(g starch or maltodextrin wet substrate) CGT enzyme is added into starch milk or a maltodextrin solution for liquefaction at 80-90° C. for 30-60 minutes;

(2) After cooling to 37-45° C., 2-4 U/(g starch or maltodextrin wet substrate) CGT enzyme is added for the cyclization reaction for 8-12 hours; after the reaction is completed, tributyrin is added, and the mass ratio of tributyrin to the starch or maltodextrin is (0.30-0.75):1;

(3) An emulsifier is added into the solution in step (2) and mixed uniformly; the emulsifier can be one or more of Tween, arabic gum, xanthan gum and the like, and the mass ratio of the addition amount of the emulsifier to the starch or maltodextrin is (0.3-0.5):1;

(4) The solution prepared in step (3) is subjected to high-speed shearing treatment, and high-speed shearing is carried out at 8000-20000 rpm for 2-5 minutes;

(5) The emulsion obtained in step (4) is subjected to homogenization to obtain a uniform and stable emulsion; the homogenization pressure is 30-40 MPa, and the homogenization frequency is 2-3;

(6) The emulsion obtained in step (5) is subjected to spray drying to obtain tributyrin powder, and the spray drying conditions are: the air inlet temperature is 180-185° C.; the air outlet temperature is 85-95° C.; and the feeding flow rate is 20-22 mL/min.

The disclosure provides inclusion complexes prepared by the method. A core material of the inclusion complexes is tributyrin, and a wall material is a mixture of cyclodextrin, dextrin and the emulsifier obtained after the enzyme acts on the substrate.

The disclosure provides application of the inclusion complexes in preparation of a substitute for antibiotic additives for feed.

The disclosure provides a substitute for antibiotic additives for feed containing the inclusion complexes.

Beneficial Effects of the Disclosure (1) The disclosure combines the processes of enzymatic synthesis of cyclodextrin and inclusion of tributyrin with cyclodextrin. The cyclodextrin and dextrin obtained after the enzyme acts on the substrate and the emulsifier added after the reaction is completed are used as the wall material to include tributyrin. The process is simple; the steps of separation and purification of cyclodextrin are omitted; and the production cost is greatly reduced.

(2) When the CGT enzyme is used to act on the starch, in addition to cyclodextrin, some oligosaccharides, dextrins and other substances are also produced. Oligosaccharides, dextrins and other substances can be used in combination with other wall material ingredients in microcapsules without separation and purification, and the cost can be greatly reduced.

(3) The tributyrin powder prepared by the disclosure has a good embedding effect; the solubility and dispersibility of tributyrin can be better improved; the storage period is prolonged; and the product quality is ensured.

DETAILED DESCRIPTION

Figure 1A:
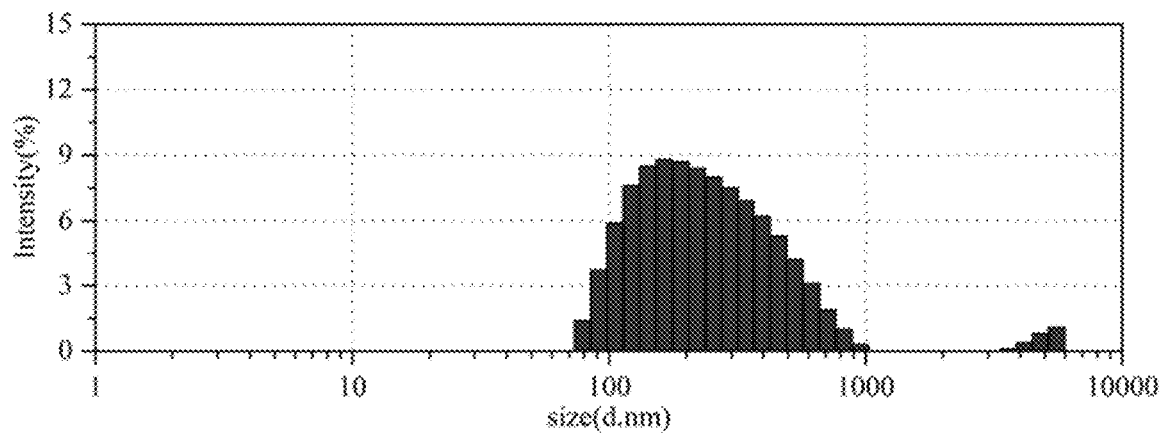
FIG. 1A: Nanoparticle size distribution diagrams of emulsions prepared from corn starch in Example 2.

1. The contents of α-cyclodextrin, β-cyclodextrin and γ-cyclodextrin in an emulsion or a powder product are measured according to the following method:

(1) A certain amount of the emulsion or powder product is taken, diluted with a 10 mM phosphate buffer (pH 6.5) for a certain times and uniformly mixed for later use.

(2) A methyl orange method is adopted for measuring the content of α-cyclodextrin: a to-be-tested solution diluted for a certain times is taken, 1.0 mL of 1.0 M hydrochloric acid solution is added, then 1.0 mL of 0.1 mM methyl orange solution prepared from 10 mM phosphate buffer is added for color developing at room temperature for 20 minutes, and the absorbance is measured at 505 nm. At the same time, the buffer is used as a blank group.

(3) The content of β-cyclodextrin is measured by adopting a phenolphthalein method: a to-be-tested solution diluted for a certain times is taken, 3.5 mL of 30 mM NaOH is added, then 0.5 mL of 0.02% (w/v) phenolphthalein solution prepared from 5 mM $Na_2CO_3$ solution is added for color developing at room temperature for 20 minutes, and the absorbance is measured at 550 nm. At the same time, the buffer is used as a blank group.

(4) The content of γ-cyclodextrin is measured by adopting a bromocresol green method: a to-be-tested solution diluted for a certain times is taken, 50 μL of 1.0 M hydrochloric acid solution is added, then 2 mL of 0.2 M citric acid buffer with the pH of 4.2 and 100 μL of 5 mM BCG solution are added for color developing at room temperature for 20 minutes, and the absorbance is measured at 615 nm. At the same time, the buffer is used as a blank group.

2. The content of tributyrin in the emulsion or powder product is measured by adopting an HPLC method:

A C18 column is selected as the chromatographic column; the column temperature is 30° C.; the mobile phase is acetonitrile-water (60:40); the flow rate is 1.0 mL/min; and the absorption wavelength is 225 nm.

Example 1 Comparison of Inclusion of Tributyrin with Cyclodextrin and Enzymatic Inclusion of Tributyrin The process of direct inclusion of tributyrin with cyclodextrin is as follows:

Tributyrin is mixed with ethanol in advance (the mass ratio of tributyrin to ethanol is 1:1), 4 wt % β-cyclodextrin is heated for dissolving and then cooled to 50° C., and then the tributyrin-ethanol solution is slowly added into the solution, wherein the mass ratio of the addition amount of tributyrin to β-cyclodextrin is (0.1-0.5):1. The mixture is shaken thoroughly and mixed uniformly, and ultrasonic treatment is carried out at 50° C. for 30 minutes. After the reaction is completed, freeze drying is carried out to obtain dry powder, and the dry powder is sealed and stored.

The preparation process of enzymatic inclusion of tributyrin is as follows:

(1) A corn starch solution with the mass concentration of 20% is used as the substrate, and the CGT enzyme is added for liquefaction at 90° C. for 60 minutes. The addition amount of the CGT enzyme is 2 U/(g starch wet substrate);

(2) The mixture is cooled to 45° C., and 2 U/(g starch wet substrate) CGT enzyme is added for cyclization reaction for 12 hours; after the reaction is completed, tributyrin is added into the system, and the mass ratio of tributyrin to the starch is (0.3-0.5):1;

(3) An emulsifier Tween-20 is added into the solution in step (2) and mixed uniformly, and the mass ratio of the emulsifier to the starch is 0.2:1;

(4) The solution prepared in step (3) is subjected to high-speed shearing treatment, and high-speed shearing is carried out at 8000-2000 rpm for 2-5 minutes;

(5) The emulsion obtained in step (4) is subjected to homogenization to obtain a uniform and stable emulsion; the homogenization pressure is 30-40 MPa, and the homogenization frequency is 2-3;

(6) The emulsion obtained in step (5) is subjected to spray drying to obtain tributyrin powder, and the spray drying conditions are: the air inlet temperature is 180-185° C.; the air outlet temperature is 85-95° C.; and the feeding flow rate is 20-22 mL/min.

Powdered oils prepared from direct inclusion of tributyrin with cyclodextrin and enzymatic inclusion of tributyrin are observed, and comparison results are shown in Table 1: in three inclusion products of tributyrin with cyclodextrins obtained by adopting different addition ratios of tributyrin and β-cyclodextrin, when the addition amount is 0.3:1 or above, the powdered oil has a greasy feel and heavy smell, and the products all have an obvious stratification phenomenon when dissolved in water at room temperature; the powdered oils prepared from enzymatic inclusion of tributyrin are uniform and stable, the smell is obviously reduced, and no stratification phenomenon occurs after the products are dissolved and placed for a period of time. Therefore, enzymatic inclusion of tributyrin has the advantages of high solubility and good smell masking.

completed, tributyrin is added into the systems, and the mass ratio of tributyrin to the starch or maltodex is 0.30:1;

(3) An emulsifier Tween-20 is added into the solutions in step (2) and mixed uniformly, and the mass ratio of the emulsifier to the starch or maltodex is 0.2:1;

(4) The solutions prepared in step (3) are subjected to high-speed shearing treatment, and high-speed shearing is carried out at 8000-2000 rpm for 2-5 minutes;

(5) The emulsions obtained in step (4) are subjected to homogenization to obtain uniform and stable emulsions; the homogenization pressure is 30-40 MPa; and the homogenization frequency is 2-3;

(6) The emulsions obtained in step (5) are subjected to spray drying to obtain tributyrin powder, and the spray drying conditions are: the air inlet temperature is 180-185° C.; the air outlet temperature is 85-95° C.; and the feeding flow rate is 20-22 mL/min.

Figure 1B:
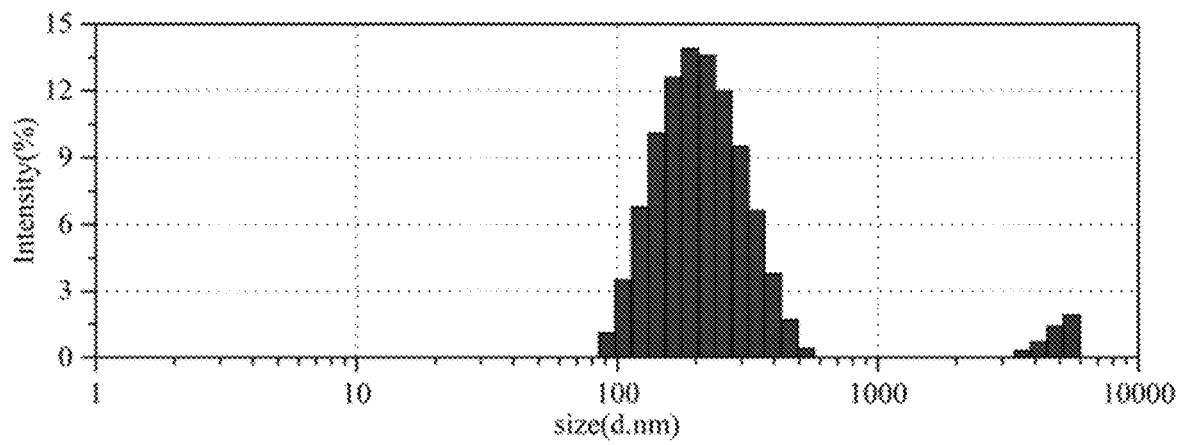
FIG. 1B: Nanoparticle size distribution diagrams of emulsions prepared from potato starch in Example 2.
Figure 1C:
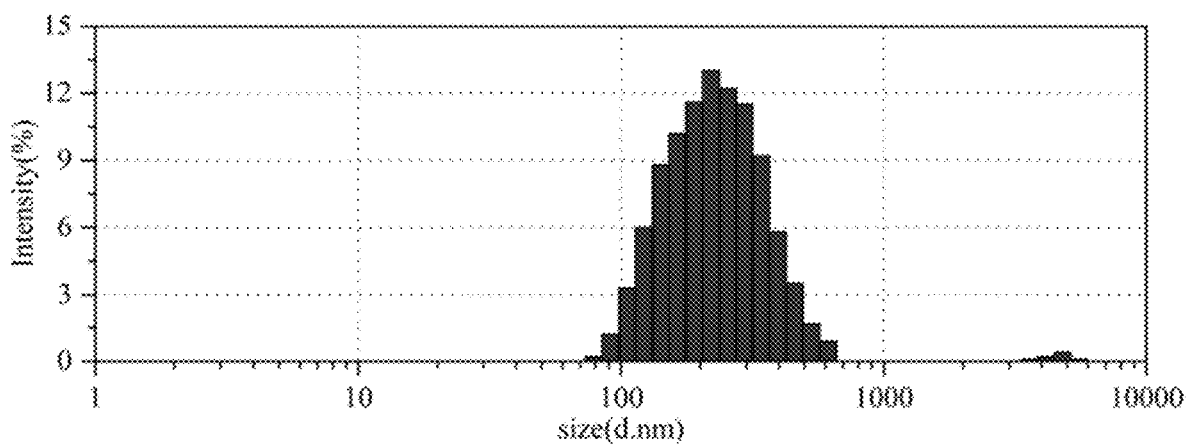
FIG. 1C: Nanoparticle size distribution diagrams of emulsions prepared from maltodextrin in Example 2.

When the corn starch, the potato starch and the maltodextrin are used as the substrates, nanoparticle size results of the obtained emulsions are shown in FIG. 1A, FIG. 1B, FIG. 1C. It can be seen from FIG. 1A, FIG. 1B, FIG. 1C that the particle sizes of the three emulsions are mainly distributed between 70 nm and 1000 nm and have good uniformity. At the same time, stratification of the three emulsions does not occur after the emulsions are placed for 15 days, and the emulsions are uniform and stable. The powder prepared after spray drying has good dispersibility, the smell is reduced, and no oil leakage phenomenon occurs after the powder is placed for 15 days.

Example 3 Influence of the Addition Amount of an Enzyme for Liquefaction on Emulsions in Preparation of Tributyrin Powder The preparation process of tributyrin powdered oils is as follows:

(1) Corn starch with the mass concentration of 20% is used as the substrate, and a CGT enzyme is added for

TABLE 1

Comparison results of inclusion of tributyrin with cyclodextrin and enzymatic inclusion of tributyrin

| Product | Inclusion of tributyrin with cyclodextrin | | | Enzymatic inclusion of tributyrin | |
|---|---|---|---|---|---|
| comparison | 0.1:1 | 0.3:1 | 0.5:1 | 0.3:1 | 0.5:1 |
| Oil content (mass fraction) | 8.8% | 21.9% | 32.9% | 15% | 21% |
| State of powder | Uniform and stable | Slightly greasy | Greasy | Uniform and stable | Uniform and stable |
| Smell of powder | Light | Heavy | Heavy | Light | Light |
| State after dissolution[1] | Stratification | Stratification | Stratification | No stratification | No stratification |

[1] The powder and water are mixed uniformly at a ratio of 0.05:1, and the state is observed after 5 days.

Example 2 Preparation of Inclusion Complexes of Tributyrin with Different Substrates The preparation process of tributyrin powdered oils is as follows:

(1) Corn starch with the mass concentration of 20%, potato starch with the mass concentration of 20% and maltodextrin (DE=10) with the mass concentration of 20% are used as the substrates respectively, and 2 U/(g starch or maltodex wet substrate) CGT enzyme is added for liquefaction at 90° C. for 60 minutes;

(2) The mixtures are cooled to 45° C.; 2 U/(g starch or maltodex wet substrate) CGT enzyme is added for cyclization reaction for 12 hours; after the reaction is liquefaction at 90° C. for 60 minutes; the addition amount of the CGT enzyme for liquefaction is 1, 1.5, 2, 3 and 4 U/(g starch wet substrate) respectively;

(2) The mixtures are cooled to 45° C.; 2 U/(g starch wet substrate) CGT enzyme is added for cyclization reaction for 12 hours; after the reaction is completed, tributyrin is added into the system, and the mass ratio of tributyrin to the starch is 0.3:1;

(3) An emulsifier Tween-20 is added into the solutions in step (2) and mixed uniformly, and the mass ratio of the emulsifier to the starch is 0.2:1;

(4) The solutions prepared in step (3) are subjected to high-speed shearing treatment, and high-speed shearing is carried out at 8000-2000 rpm for 2-5 minutes;

(5) The emulsions obtained in step (4) are subjected to homogenization to obtain uniform and stable emulsions; the homogenization pressure is 30-40 MPa; and the homogenization frequency is 2-3.
(6) The emulsions obtained in step (5) are subjected to spray drying to obtain tributyrin powder, and the spray drying conditions are: the air inlet temperature is 180-185° C.; the air outlet temperature is 85-95° C.; and the feeding flow rate is 20-22 mL/min.

Figure 2:
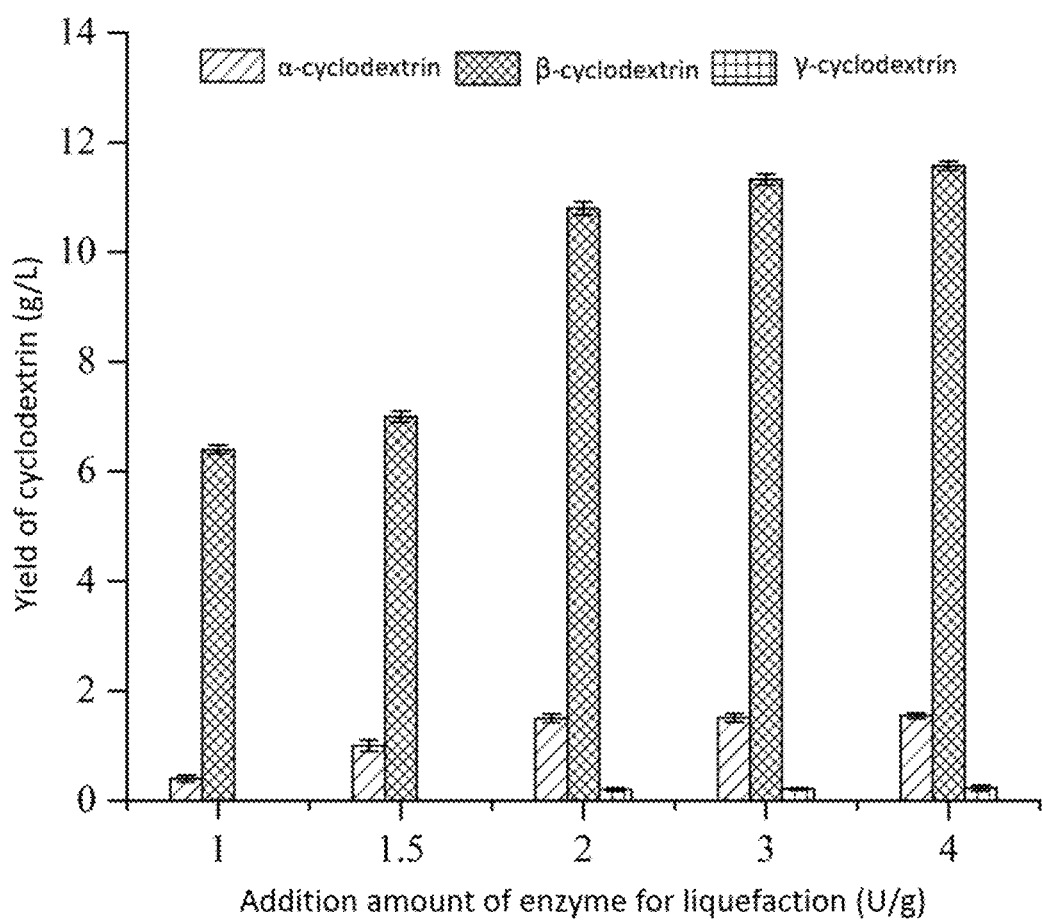
FIG. 2: A diagram showing the influence of the addition amount of an enzyme in liquefaction on the yield of cyclodextrin in Example 3.

Yield results of three cyclodextrins in the solutions obtained by adding different amounts of the enzyme for liquefaction are shown in FIG. 2. It can be seen from FIG. 2 that when the addition amount of the CGT enzyme in the liquefaction process is relatively low (1 and 1.5 U/g), the content of the main product β-cyclodextrin is obviously low, and γ-cyclodextrin is not detected; when the addition amount is 2, 3 and 4 U/g, the yield of the main product β-cyclodextrin reaches 10.8, 11.2 and 11.6 g/L respectively. At the same time, it is found in liquefaction and subsequent cyclization process that when the addition amount of the enzyme is lower than or equal to 1.5 U/g, the system viscosity is high, which may cause low cyclodextrin yield due to insufficient stirring in the cyclization process. In addition, the high system viscosity is not conducive to subsequent emulsification mixing, shearing, homogenization and other operations. When the addition amount of the enzyme is 2, 3 and 4 U/g, the prepared solutions have suitable viscosity and are easy to stir; subsequent operations such as emulsification mixing, shearing and homogenization can be carried out; powder obtained after spray drying has good dispersibility; the smell is reduced; and there is no oil leakage phenomenon after the powder is placed for 15 days.

Example 4 Influence of Homogenization Pressure on Emulsions in Preparation Process of Tributyrin Powder The preparation process of tributyrin powdered oils is as follows:
(1) Corn starch with the mass concentration of 20% is used as the substrate, and a CGT enzyme is added for liquefaction at 90° C. for 60 minutes; the addition amount of the CGT enzyme for liquefaction is 2 U/(g starch wet substrate);
(2) The mixture is cooled to 45° C.; 2 U/(g starch wet substrate) CGT enzyme is added for cyclization reaction for 12 hours; after the reaction is completed, tributyrin is added into the system, and the mass ratio of tributyrin to the starch is 0.30:1;
(3) An emulsifier Tween-20 is added into the solution in step (2) and mixed uniformly, and the mass ratio of the emulsifier to the starch is 0.2:1;
(4) The solution prepared in step (3) is subjected to high-speed shearing treatment, and high-speed shearing is carried out at 8000-2000 rpm for 2-5 minutes;
(5) The emulsion obtained in step (4) is subjected to homogenization to obtain uniform and stable emulsions; the homogenization pressure is 20-30 MPa, 30-40 MPa and 40-50 MPa respectively; and the homogenization frequency is 2-3;
(6) The emulsions obtained in step (5) are subjected to spray drying to obtain tributyrin powder, and the spray drying conditions are: the air inlet temperature is 180-185° C.; the air outlet temperature is 85-95° C.; and the feeding flow rate is 20-22 mL/min.

Figure 3A:
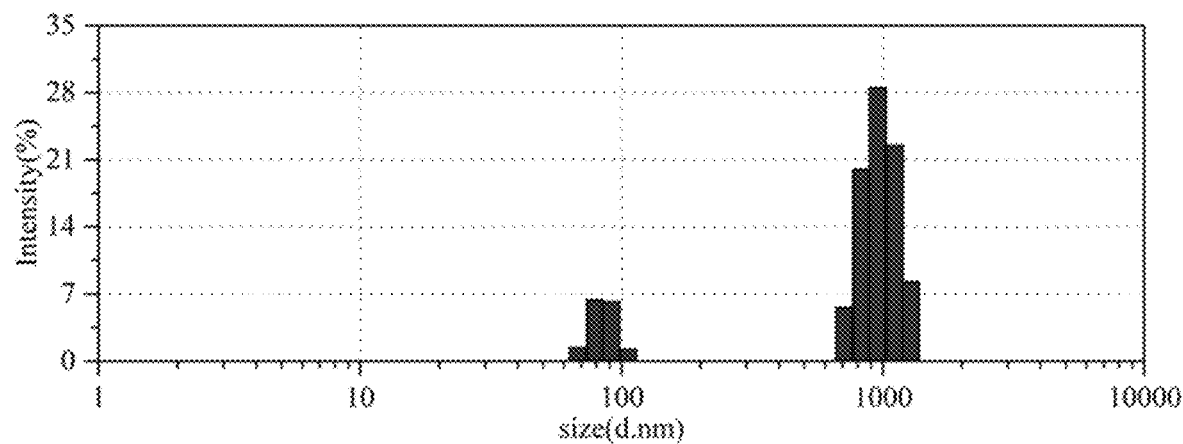
FIG. 3A: Nanoparticle size distribution diagrams of emulsions prepared under 20-30 MPa in Example 4.
Figure 3B:
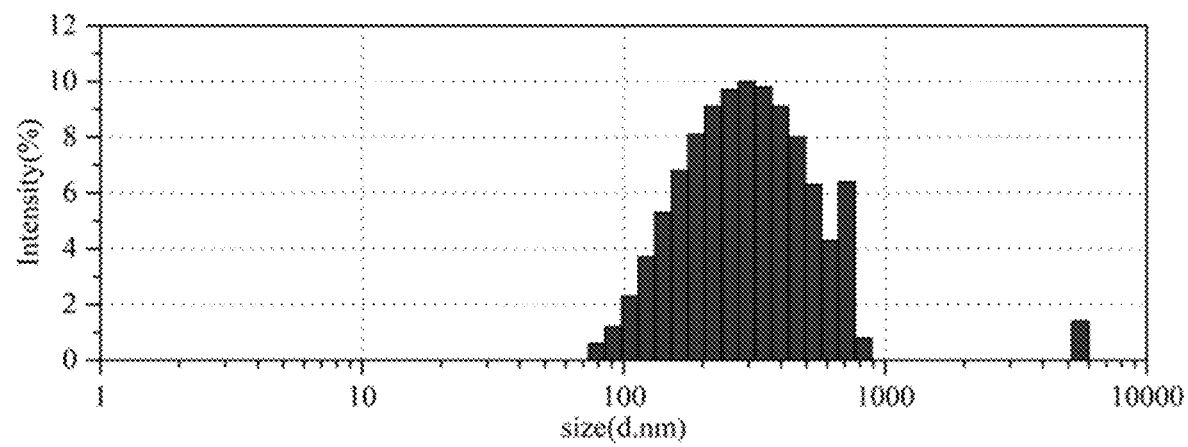
FIG. 3B: Nanoparticle size distribution diagrams of emulsions prepared under 30-40 MPa in Example 4.
Figure 3C:
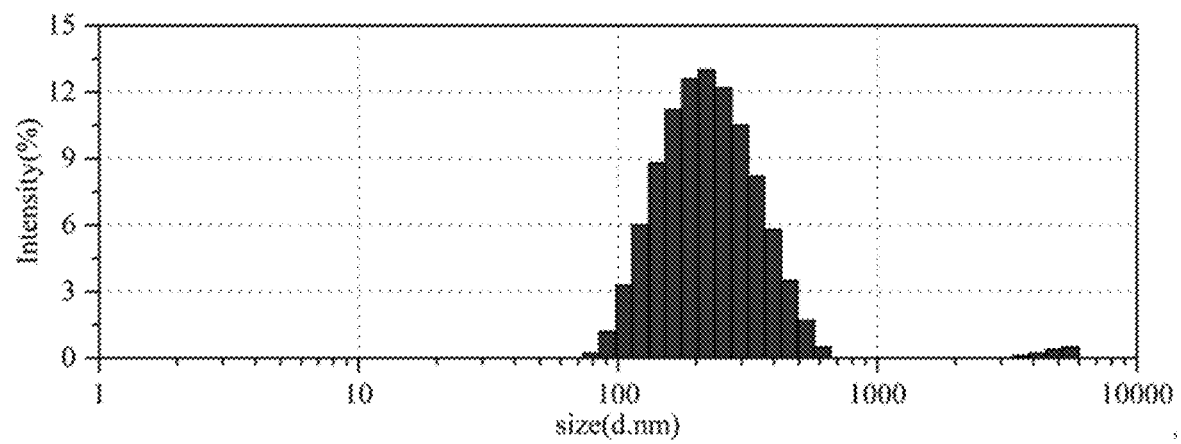
FIG. 3C: Nanoparticle size distribution diagrams of emulsions prepared under 40-50 MPa in Example 4.

The nanometer particle size distribution of the emulsions obtained under different homogenization pressures is shown in FIG. 3A, FIG. 3B, FIG. 3C. It can be seen from FIG. 3A, FIG. 3B, FIG. 3C that the higher the homogenization pressure, the smaller the main distribution particle size of the emulsion. Under low homogenization pressure (20-30 MPa), the particle size distribution is relatively uneven and mainly concentrated at 1000 nm. When the homogenization pressure reaches 30 MPa or above, the homogenized emulsions are in normal distribution. When the homogenization pressure is 40-50 Mpa, although the particle sizes of the emulsions are smaller, the improvement is not large, and the requirements for homogenizer equipment are high. Therefore, it is appropriate to select the homogenization pressure of 30-40 MPa.

Example 5 Influence of the Addition of an Emulsifier on Preparation of Tributyrin Powder The preparation process of tributyrin powdered oils is as follows:
(1) Corn starch with the mass concentration of 20% is used as the substrate, and a CGT enzyme is added for liquefaction at 90° C. for 60 minutes; the addition amount of the CGT enzyme for liquefaction is 2 U/(g starch wet substrate);
(2) The mixture is cooled to 45° C.; 2 U/(g starch wet substrate) CGT enzyme is added for cyclization reaction for 12 hours; after the reaction is completed, tributyrin is added into the system, and the mass ratio of tributyrin to the starch is 0.30:1;
(3) An emulsifier Tween-20 is added into the solution in step (2) and mixed uniformly; the mass ratio of the emulsifier to the starch is 0.2:1; and the solution in step (2) without the addition of the emulsifier is used as a reference;
(4) The solutions prepared in step (3) are subjected to high-speed shearing treatment, and high-speed shearing is carried out at 8000-2000 rpm for 2-5 minutes;
(5) The emulsions obtained in step (4) are subjected to homogenization to obtain uniform and stable emulsions; the homogenization pressure is 30-40 MPa; and the homogenization frequency is 2-3;
(6) The emulsions obtained in step (5) are subjected to spray drying to obtain tributyrin powder, and the spray drying conditions are: the air inlet temperature is 180-185° C.; the air outlet temperature is 85-95° C.; and the feeding flow rate is 20-22 mL/min.

Figure 4A:
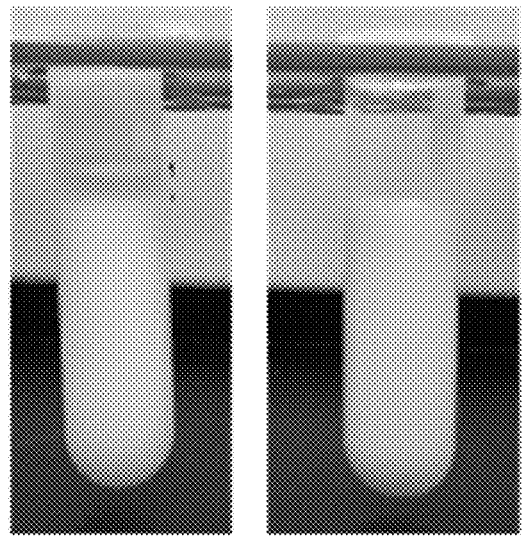
FIG. 4A: Diagrams showing the states of emulsions with and without the addition of an emulsifier in Example 5.
Figure 4B:
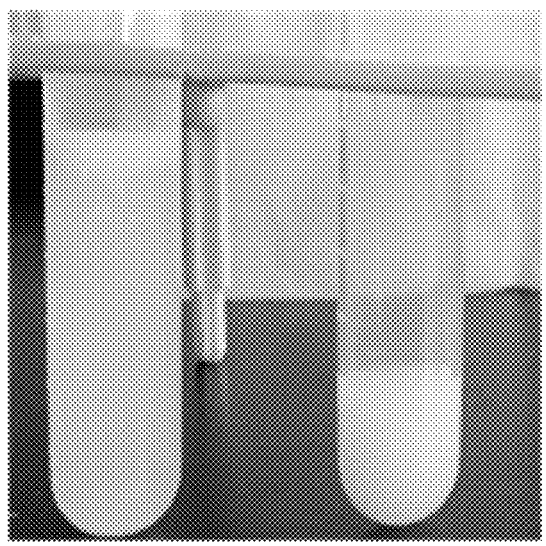
FIG. 4B: Diagrams showing the states of dissolved powdered oils emulsions with and without the addition of an emulsifier in Example 5.

The emulsions with and without the addition of the emulsifier and the solutions of dissolved powdered oils are placed for 24 hours and compared in state, and results are shown in FIG. 4A and FIG. 4B. It can be clearly seen that when no emulsifier is added, the emulsion and the solution of the dissolved powdered oil have a stratification phenomenon after being placed for a period of time. The emulsion prepared by adding the emulsifier and the powdered oil are both uniform and stable and have no stratification.

Example 6 Influence of the Addition Amount of Tributyrin on Preparation of Tributyrin Powder The preparation process of tributyrin powdered oils is as follows:
(1) Corn starch with the mass concentration of 20% is used as the substrate, and a CGT enzyme is added for liquefaction at 90° C. for 60 minutes; the addition amount of the CGT enzyme for liquefaction is 2 U/(g starch wet substrate);
(2) The mixture is cooled to 45° C.; 2 U/(g starch wet substrate) CGT enzyme is added for cyclization reaction for 12 hours; after the reaction is completed, tributyrin is added into the system, and the raw material ratio (mass ratio) of tributyrin to the starch is 0.30:1, 0.50:1, 0.75:1 and 1:1 respectively;
(3) An emulsifier Tween-20 is added into the solutions in step (2) and mixed uniformly; the mass ratio of the emulsifier to the starch is 0.2:1; and a solution in step (2) without the addition of the emulsifier is used as a reference;
(4) The solutions prepared in step (3) are subjected to high-speed shearing treatment, and high-speed shearing is carried out at 8000-2000 rpm for 2-5 minutes;
(5) The emulsions obtained in step (4) are subjected to homogenization to obtain uniform and stable emulsions; the homogenization pressure is 30-40 MPa; and the homogenization frequency is 2-3;
(6) The emulsions obtained in step (5) are subjected to spray drying to obtain tributyrin powder, and the spray drying conditions are: the air inlet temperature is 180-185° C.; the air outlet temperature is 85-95° C.; and the feeding flow rate is 20-22 mL/min.

Table 2 shows the measured oil content and state results of powdered oils prepared under different addition amounts. It can be seen from Table 2 that when the mass ratio of tributyrin to the starch is (0.30-0.75):1, the obtained emulsion is stable, and the state and solubility of the powdered oil are both good. With the increase of the addition amount of tributyrin, the oil content is higher and higher. But when the mass ratio of tributyrin to the starch is 1:1, the emulsion has a stratification phenomenon, and the powder is slightly greasy; the oil content is increased slightly, but the increase is not large. The main reason may be that when too much tributyrin is added, the embedding effect of the system is not good, and the unembedded part is more unstable in the spray drying process and is likely to be decomposed by heat.

TABLE 2

The oil contents and states of powdered oils prepared under different oil addition amounts

| Oil addition amount (Glyceride:starch) | 0.30:1 | 0.50:1 | 0.75:1 | 1:1 |
|---|---|---|---|---|
| Oil content | 15% | 20% | 32.8% | 35.2% |
| Emulsion stability | No stratification | No stratification | No stratification | Light stratification |
| State of powder | Uniform and stable | Uniform and stable | Uniform and stable | Uniform and slightly greasy |
| Solubility | Good | Good | Good | Good |

What is claimed is:

1. A method of enzymatic preparation of inclusion complexes of tributyrin, comprising:
(a) preparing starch milk or a maltodextrin solution as a raw material, wherein a mass concentration of the starch milk or maltodextrin solution is 15% to 30%, and wherein the starch milk is an aqueous suspension of starch from one or more of corn starch, waxy corn starch, potato starch, rice starch, cassava starch, and wheat starch;
(b) adding an enzyme into the starch milk or maltodextrin solution for liquefaction reaction and cyclization reaction to form cyclodextrin, wherein the enzyme is cyclodextrin glucosyltransferase which catalyzes cyclization of glucan polymers in the starch milk to form the cyclodextrin, and wherein liquefaction is performed at a temperature of 80° C. to 90° C.; and
(c) adding tributyrin and an emulsifier so that tributyrin is included,
wherein there is no separation and/or purification of the cyclodextrin between steps (b) and (c).

2. The method according to claim 1, wherein maltodextrin in the maltodextrin solution is maltodextrin from a starch source with a dextrose equivalent (DE) value of 5 to 25.

3. The method according to claim 1, further comprising: (d) mixing, (e) shearing, (r) homogenizing, and (g) spray drying.

4. The method according to claim 1, wherein a mass ratio of tributyrin to starch in the starch milk or maltodextrin in the maltodextrin solution is (0.30-0.75):1.

5. The method according to claim 1, wherein in the liquefaction reaction, an addition amount of cyclodextrin glucosyltransferase is 2 to 4 Unit/gram starch or maltodextrin wet substrate, and the liquefaction reaction time is 30 to 60 minutes.

6. The method according to claim 1, wherein in the cyclization reaction, an addition amount of cyclodextrin glucosyltransferase is 2 to 4 Unit/gram starch or maltodextrin wet substrate, a cyclization temperature is 45° C., and the cyclization reaction time is 8 to 12 hours.

7. The method according to claim 1, wherein the emulsifier is any one or more of Tween, arabic gum and xanthan gum, and a mass ratio of the emulsifier to starch in the starch milk or maltodextrin in the maltodextrin solution is (0.3-0.5):1.

8. The method according to claim 3, wherein a shearing speed is 8000 rpm to 20000 rpm, and the shearing time is 2 to 5 minutes; a homogenization pressure is 30 MPa to 40 MPa, and a homogenization frequency is 2 to 3; and spray drying conditions are under: an air inlet temperature is 180° C. to 185° C., an air outlet temperature is 85° C. to 95° C., and a feeding flow rate is 20 mL/min to 22 mL/min.

* * * * *